United States Patent
Driscoll et al.

(10) Patent No.: US 10,349,864 B2
(45) Date of Patent: Jul. 16, 2019

(54) METHODS AND SYSTEM FOR PERFORMING MAGNETIC INDUCTION TOMOGRAPHY

(71) Applicant: Elwha LLC, Bellevue, WA (US)

(72) Inventors: Tom Driscoll, San Diego, CA (US); David R. Smith, Durham, NC (US); Yaroslav A. Urzhumov, Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 892 days.

(21) Appl. No.: 14/689,871

(22) Filed: Apr. 17, 2015

(65) Prior Publication Data

US 2016/0305910 A1 Oct. 20, 2016

(51) Int. Cl.
*G01V 3/08* (2006.01)
*A61B 5/05* (2006.01)
*A61B 5/00* (2006.01)

(52) U.S. Cl.
CPC .......... *A61B 5/0522* (2013.01); *A61B 5/0037* (2013.01); *G01V 3/08* (2013.01); *G01V 3/081* (2013.01)

(58) Field of Classification Search
CPC ..................................................... G01N 27/72
USPC ........................................................ 324/239
See application file for complete search history.

(56) References Cited

U.S. PATENT DOCUMENTS

| 8,125,220 | B2 | 2/2012 | Igney et al. |
| 8,808,190 | B2 * | 8/2014 | Rosell Ferrer ......... A61B 5/053 600/508 |
| 2008/0258717 | A1 * | 10/2008 | Igney ................... A61B 5/0522 324/222 |
| 2011/0313277 | A1 * | 12/2011 | Igney ...................... A61B 5/05 600/410 |

FOREIGN PATENT DOCUMENTS

| EP | 2 332 463 | 6/2011 | |
| EP | 2 333 587 | 6/2011 | |
| WO | WO-2008018018 A2 * | 2/2008 | ............... A61B 5/05 |

(Continued)

OTHER PUBLICATIONS

Brunner et al., Reconstruction of the shape of conductivity spectra using differential multi-frequency magnetic induction tomography, Institute of Physics Publishing, Physiological Measurement 27 (2006) S237-S248, 13 pages.

(Continued)

*Primary Examiner* — Douglas X Rodriguez
(74) *Attorney, Agent, or Firm* — Foley & Lardner LLP

(57) ABSTRACT

Methods and system for performing magnetic induction tomography imaging of an object are provided. An apparatus includes an array of unit cells and a control circuit coupled to the array of unit cells. The array of unit cells can generate a first magnetic field using an excitation pattern in the direction of a target object and sense a second magnetic field induced in the target object by the first magnetic field. The control circuit can determine a minimum of the first magnetic field. The minimum may correspond to a higher (Continued)

conductivity region of the target object. The control circuit can adjust the excitation pattern based on the higher conductivity region of the target object.

10 Claims, 7 Drawing Sheets

(56) References Cited

FOREIGN PATENT DOCUMENTS

WO   WO-2009/144461   12/2009
WO   WO-2010/003162   1/2010

OTHER PUBLICATIONS

Freiberger et al., The AGILE library for image reconstruction in biomedical sciences using graphics card hardware acceleration, Austrian Science Fund, SFB-Report No. 2012-009, Apr. 2012, 13 pages.
Griffiths et al., Magnetic Induction Tomography—A measuring system for biological tissues, Annals New York Academy of Sciences, no date, 11 pages.
Griffiths, Chapter 8: Magnetic Induction Tomography, Electrical Impedance Tomography: Methods, History and Applications, edited by David S. Holder, 2004, 27 pages.
Griffiths, Magnetic induction tomography, Institute of Physics Publishing, Meas. Sci. Technol. 12 (2001) 11260131131, 6 pages.
Gursoy et al., A Marker Belt Design to Eliminate the Motion Artifacts in Magnetic Induction Tomography, Biomedical Engineering Meeting (BIYOMUT), 2010 15th National held Apr. 2010, published by IEEE, 3 pages.
Gursoy et al., Enhancing Impedance Imaging Through Multimodal Tomography, IEEE Transactions on Biomedical Engineering, vol. 58, No. 11, Nov. 2011, 10 pages.
Gursoy et al., Feasibility of lung imaging using magnetic induction tomography, Austrian Science Fund SFB-Report No. 2009013013, Apr. 2009, 10 pages.
Gursoy et al., Imaging artifacts in magnetic induction tomography caused by the structural incorrectness of the sensor model, IOP Publishing, Meas. Sci. Technol. 22 (2011) 015502, 10 pages.
Gursoy et al., Magnetic induction pneumography: a planar coil system for continuous monitoring of lung function via contactless measurements, Journal of Electric Bioimpedance, vol. 1, pp. 5601362, 2010, 7 pages.
Gursoy et al., Optimum Receiver Array Design for Magnetic Induction Tomography, IEEE Transactions on Biomedical Engineering, vol. 56, No. 5, May 2009, 7 pages.
Gursoy et al., Reconstruction artefacts in magnetic induction tomography due to patient's movement during data acquisition, IOP Publishing, Physiological Measurement 30 (2009) S165-S174, 11 pages.
Gursoy et al., The effect of receiver coil orientations on the imaging performance of magnetic induction tomography, IOP Publishing, Measurement Science and Technology 20 (2009) 105505, 9 pages.
Korjenevsky et al., Magnetic induction tomography: experimental realization, Physiol. Meas. 21 (2000) 89-94, 6 pages.
Korjenevsky et al., Progress in Realization of Magnetic Induction Tomography, Institute of Radioengineering and Electronics, Russian Academy of Sciences, Moscow 103907, Russia, 7 pages.
Kyle et al., Bioelectrical impedance analysis part I: review of principles and methods, Clinical Nutrition (2004) 23, 1226-1243, 18 pages.
Kyle et al., Bioelectrical impedance analysis part II: utilization in clinical practice, Clinical Nutrition (2004) 23, 1430-1453, 24 pages.
Merwa et al., Detection of brain oedema using magnetic induction tomography: a feasibility study of the likely sensitivity and detectability, Institute of Physics Publishing, Physiol. Meas. 25 (2004) 347-354, 8 pages.
Merwa et al., Numerical solution of the general 3D eddy current problem for magnetic induction tomography (spectroscopy), Institute of Physics Publishing, Physiol. Meas. 24 (2003) 545-554, 11 pages.
Merwa et al., Solution of the inverse problem of magnetic induction tomography (MIT), Institute of Physics Publishing, Physiol. Meas. 26 (2005) S241-S250, 11 pages.
Rosell et al., Sensitivity maps and system requirements for magnetic induction tomography using a planar gradiometer, Institute of Physics Publishing, Physiological Measurement 22 (2001) 121-130, 11 pages.
Scharfetter et al., A new type of gradiometer for the receiving circuit of magnetic induction tomography (MIT), Institute of Physics Publishing, Physiol. Meas. 26 (2005) S307-S318, 13 pages.
Scharfetter et al., Biological Tissue Characterization by Magnetic Induction Spectroscopy (MIS): Requirements and Limitations, IEEE Transactions on Biomedical Engineering, vol. 50, No. 7, Jul. 2003, 11 pages.
Scharfetter et al., Fat and Hydration Monitoring by Abdominal Bioimpedance Analysis: Data Interpretation by Hierarchical Electrical Modeling, IEEE Transactions on Biomedical Engineering, vol. 52, No. 6, Jun. 2005, 8 pages.
Scharfetter et al., Magnetic induction tomography: hardware for multi-frequency measurements in biological tissues, Institute of Physics Publishing, Physiol. Meas. 22 (2001) 131-146, 16 pages.
Scharfetter et al., Reduction of low-frequency noise in magnetic induction tomography systems, Austrian Science Fund, SFB-Report No. 2009-018, May 2009, 8 pages.
Scharfetter et al., Single-Step 3-D Image Reconstruction in Magnetic Induction Tomography: Theoretical Limits of Spatial Resolution and Contrast to Noise Ratio, Annals of Biomedical Engineering, vol. 34, No. 11, Nov. 2006 pp. 1786-1798, 13 pages.
Scharfetter et al., Spectroscopic 16 channel magnetic induction tomograph: The new Graz MIT system, Austrian Science Fund, SFB-Report No. 2007-010, Dec. 2007, 6 pages.
Woo et al., Chapter 9: Magnetic resonance electrical impedance tomography (MREIT), Electrical Impedance Tomography: Methods, History and Applications, edited by David S. Holder, 2004, 56 pages.

\* cited by examiner

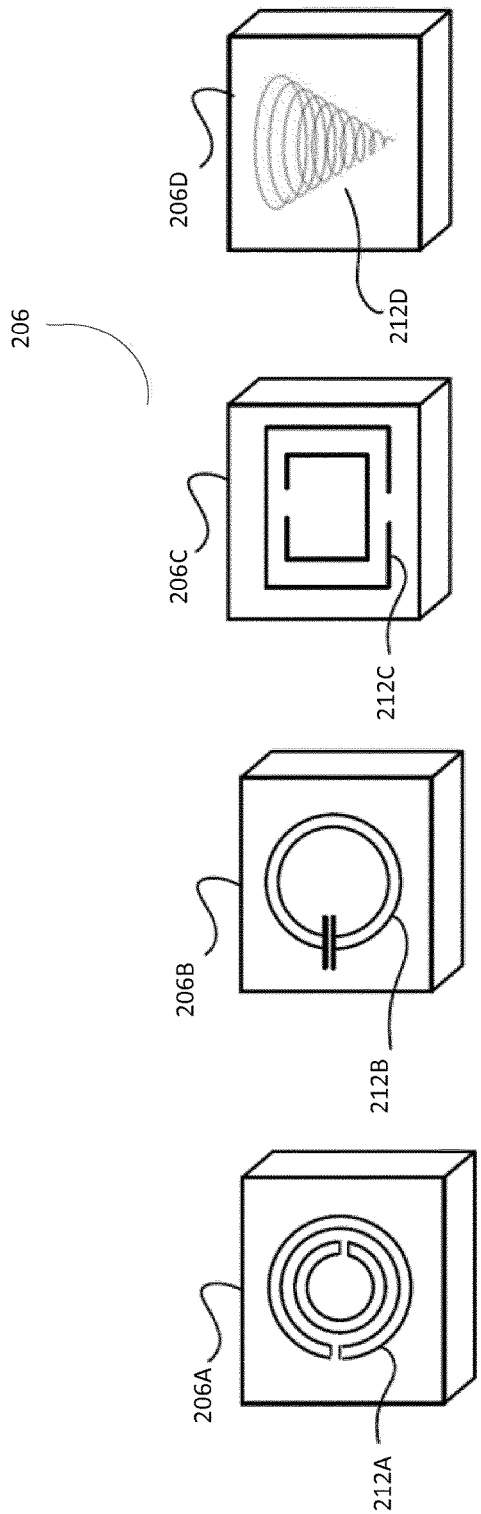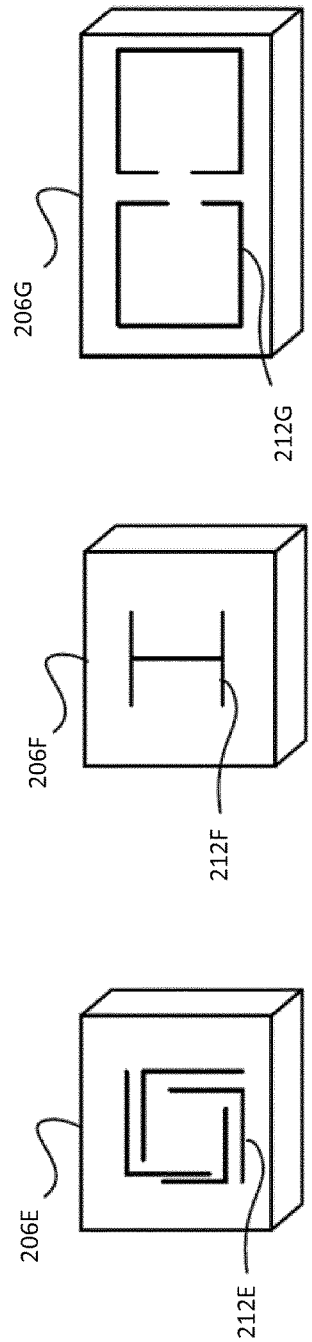

METHODS AND SYSTEM FOR PERFORMING MAGNETIC INDUCTION TOMOGRAPHY

BACKGROUND

Medical imaging is the technique, process and art of creating visual representations of the interior of a body for clinical analysis and medical intervention. Medical imaging seeks to reveal internal structures hidden by the skin and bones without disturbing them, as well as to diagnose and treat disease. Some examples of medical imaging techniques include nuclear magnetic resonance imaging and magnetic induction tomography.

SUMMARY

In one aspect, a first apparatus for performing magnetic induction tomography imaging of a target object is provided. The apparatus includes an array of unit cells and a control circuit coupled to the array of unit cells. Each unit cell may include a pattern of conducting lines and the array of unit cells can be configured to generate a first magnetic field based on an excitation pattern and sense a second magnetic field induced in a target object. The control circuit can be configured to provide the excitation pattern to the array of unit cells such that the first magnetic field has a minimum corresponding to an estimated higher conductivity region of the target object.

In another aspect, a second apparatus for performing magnetic induction tomography imaging of a target object is provided. The apparatus includes an array of unit cells and a control circuit coupled to the array of unit cells. Each unit cell may include a pattern of conducting lines and the array of unit cells can be configured to generate a first magnetic field based on an excitation pattern at a first time t and sense a second magnetic field induced in a target object at a second time t+$\Delta$t. The control circuit can be configured to provide the excitation pattern to the array of unit cells such that the first magnetic field has a minimum corresponding to an estimated higher conductivity region of the target object.

In another aspect, a third apparatus for performing magnetic induction tomography imaging of a target object is provided. The apparatus includes an array of unit cells and a control circuit coupled to the array of unit cells. Each unit cell may include a pattern of conducting lines and the array of unit cells can be configured to generate a first magnetic field based on an excitation pattern at a plurality of frequencies and sense a second magnetic field induced in a target object at the plurality of frequencies. The control circuit can be configured to provide the excitation pattern to the array of unit cells such that the first magnetic field has a minimum corresponding to an estimated higher conductivity region of the target object.

In another aspect, a first method for performing magnetic induction tomography imaging of an object is provided. The method includes an array of unit cells generating a first magnetic field using an excitation pattern in the direction of a target object and sensing a second magnetic field induced in the target object by the first magnetic field. The method further includes a control circuit determining a feasible magnetic field configuration with a local or global minimum of magnetic field intensity. The location of the minimum may correspond to a higher conductivity region of the target object. The method further includes the control circuit adjusting the excitation pattern based on the estimated conductivity distributions of the target object.

In another aspect, a second method for performing magnetic induction tomography imaging of an object is provided. The method includes an array of unit cells generating a first magnetic field using an excitation pattern in the direction of a target object at a first time t and sensing a second magnetic field induced in the target object by the first magnetic field at a second time t+$\Delta$t. The method further includes a control circuit determining a feasible magnetic field configuration with a local or global minimum of magnetic field intensity. The location of the minimum may correspond to a higher conductivity region of the target object. The method further includes the control circuit adjusting the excitation pattern based on the estimated conductivity distributions of the target object.

In another aspect, a third method for performing magnetic induction tomography imaging of an object is provided. The method includes an array of unit cells generating a first magnetic field using an excitation pattern in the direction of a target object at a plurality of frequencies and sensing a second magnetic field induced in the target object by the first magnetic field at the plurality of frequencies. The method further includes a control circuit determining a feasible magnetic field configuration with a local or global minimum of magnetic field intensity. The location of the minimum may correspond to a higher conductivity region of the target object. The method further includes the control circuit adjusting the excitation pattern based on the estimated conductivity distributions of the target object.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIGS. 2A-2G depict illustrative examples of unit cells, according to several embodiments.

DETAILED DESCRIPTION

Figure 1:
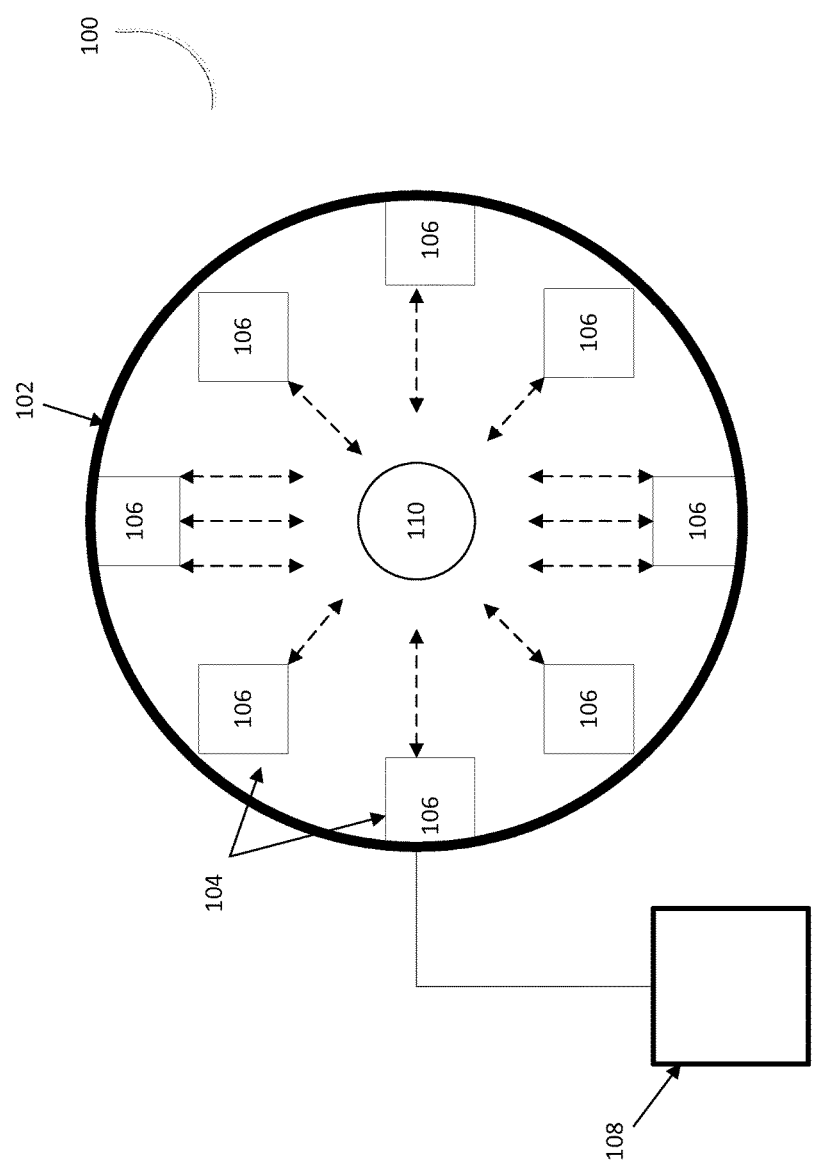
FIG. 1 is a block diagram of a system for performing magnetic induction tomography imaging of an object, according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the scope of the subject matter presented here.

The present disclosure is directed towards system and methods for imaging an object using magnetic induction tomography (MIT). MIT is a three-dimensional imaging technique with potential applications in security imaging, medical imaging and subsurface imaging (geological, petrophysical, and etc.). MIT can utilize low-frequency, for example less than 100 MHz, electromagnetic fields with dominant magnetic component, typically generated by coils and other magnetic dipole antennas or sources.

In medical imaging, MIT can be used as a continuous, non-invasive imaging technique for various parts of the human body. MIT does not use ionizing radiation, and its only effect on the patient is tissue heating in proportion to the specific absorption rate (SAR), an effect that is biologically mitigated by blood perfusion in a living tissue. Additionally, MIT does not require contact of a sensor to the object to be imaged. For example, MIT can be used to image organs and objects within the human body, for security screening (e.g., airport check points) or medical diagnostics. MIT imaging techniques produce a reconstructed image showing the electromagnetic properties of an object. In MIT imaging, a magnetic field is applied to an object from one or more unit cells to induce eddy currents in the object. The presence of conductive and/or permeable material can distort the magnetic field, and the distorted magnetic field or response of the object to the applied magnetic field is sensed by receiving unit cells. The object can be excited by the magnetic field one or more times until a reconstructed image with a desired spatial resolution is achieved. In an embodiment, each time the object is excited, a new excitation pattern is used to generate a magnetic field that may be different from a previous and/or subsequent scan. For example, a second scan may provide a near null magnetic field to areas that were indicated to have high conductivity in a first scan.

In an embodiment, the contrast of MIT images in biological tissues is almost entirely due to the (complex) electrical conductivity. At such low frequencies, complex conductivity, $\sigma_c = \sigma + i\omega\epsilon_r$, is predominantly real in live tissues, although its phase may vary significantly in other substances, such as rocks and soils. Multi-frequency, with several discrete excitation frequencies, or hyperspectral (e.g., broad-spectrum) versions of MIT can provide a second contrast mechanism by mapping both the real and imaginary parts or, equivalently, the magnitude and phase of complex conductivity. One variant of MIT is relaxation time imaging. In relaxation time imaging secondary magnetic fields of the decaying (relaxing) electrical currents induced at a previous time t are imaged at several later times, for example $t+\Delta t$, $t+2\Delta t$, etc., which can also provide contrast mechanisms beyond electrical conductivity. The relaxation time measurements can reveal the real dielectric constant and its distribution in the object. In geophysical applications, magnetic susceptibility of the medium can be non-negligible due to the presence of iron and other magnetic elements, which enables additional contrast mechanisms. In one aspect, the present disclosure is directed to bio-imaging applications of MIT, and provides systems and methods for enhancing the dynamic range and spatial resolution of the MIT technique. In bio-imaging applications, injection of contrast agents into the tissue can be used to further enhance the contrast of MIT images.

FIG. 1 depicts a magnetic induction tomography (MIT) system 100. In an embodiment, MIT system 100 includes housing structure 102 and an array 104 of unit cells 106. The MIT system 100 can be used for continuous, non-invasive imaging of an object 110. In some embodiments, the object 110 can include various parts of the human body, such as an organ or internal cavity. The object 110 may be a target object, for example, the target object may be human body, a portion of a human body, a geological formation, or a volume adjacent to a borehole. In an embodiment, the MIT system 100 is configured to control magnitudes and phases of excitation elements. The MIT system 100 can generate a magnetic field with a predefined magnitude, direction, and phase and excite a large array of elements simultaneously, which can lead to enhanced dynamic range and improved spatial resolution of a reconstructed image.

In an embodiment, the MIT system 100 includes the housing 102. The housing 102 is a support device or structure, formed to support and protect the array of unit cells 104. The housing 102 may include at least one of active metamaterial, powered metamaterial, current-driven metamaterial or voltage controlled metamaterial. In some embodiments, the housing is configured to have a round or spherical shape. However, it should be noted that the housing 102 can be formed into any shape including a square, rectangle, octagonal, etc. The housing 102 includes a connection point for the array 104 to connect to a control circuit 108. The housing 102 can be configured to receive an excitation pattern or current from the control circuit 108 and provide or transmit the excitation pattern or current to the array of unit cells 104. In some embodiments, the housing 102 includes a hollow core or a bore to allow coupling of unit cells 106.

In an embodiment, the MIT system 100 serves as both a transmitter (e.g., source) of alternating magnetic fields and receiver of alternating magnetic flux, and includes auxiliary electronic circuitry for feeding the transmitter and translating the induced electromotive force (emf) into digitized magnitudes and phases. The auxiliary electronic circuitry may include a digital to analog converter (DAC), analog to digital converter (ADC), or amplifiers. To transmit and receive the magnetic fields, the MIT system 100 includes the array 104 of unit cells 106.

In an embodiment, the array 104 is a two-dimensional array of identical or similar unit cells 106. The MIT system 100 may use an aperiodic array 104 of unit cells 106. In other embodiments, the MIT system 100 can use a curved array 104 of unit cells 106. The array 104 can be formed in planar formation, curved formation, or a random formation. The array 104 can be coupled to the housing 102 to form the MIT system 100. In some embodiments, the unit cells 106 are coupled to an inner surface of the housing 102 to form a spherical array in which the unit cells 106 are configured to transmit and receive a magnetic field to the center of the housing 102. For example, and as illustrated in FIG. 1, the object 110 may be placed in a center bore of the housing 102 with the array 104 of unit cells 106 directed at the object 110 to provide a magnetic field and sense a response of the object 110 to the magnetic field.

The array 104 can include multiple layers of unit cells 106. For example, in one embodiment, the array of unit cells 104 includes two or more layers of unit cells 106. The unit cells 106 may be stacked on top of each other to form a first layer and a second layer in the MIT system 100. The stack of unit cells 106 can be configured to measure a gradient of magnetic field components in the direction normal to its surface. In one embodiment, each layer in the stack of unit cells 106 includes resonators of all three mutually orthogonal orientations configured to sense the normal gradient of all three components of a magnetic field. In other embodiments, the unit cells 106 include non-resonant elements such as contiguous (non-split) coils or rings. In an embodiment, each unit cell 106 in the array of unit cells 104 may be a superconducting quantum inference device (SQUID), for example each unit cell 106 may be a quantum-mechanical magnetic field sensor. In other embodiments, each unit cell 106 may be at least one of an optical magnetometer or a Hall effect magnetometer. The unit cells 106 may be configured as a magnetometer as either a vector type (i.e. capable of measuring the magnetic field and its direction, or all three components of magnetic field), or scalar type (i.e. capable of measuring only the magnitude of the magnetic field). The unit cells 106 may be a non-inductive vector magnetometer, including at least one of: quantum-mechanical magnetic flux sensors (SQUID), Faraday force magnetometers, optical magnetometers, magneto-optic Kerr effect magnetometers, Faraday rotation magnetometers, Zeeman shift spectrometers, Hanle effect magnetometers, or Hall effect magnetometers. In some embodiments, the array of unit cells 106 includes scalar magnetometers of any of the following types: proton precession magnetometer, Overhauser effect magnetometer, Cesium/Potassium vapor magnetometer, or Bell-Bloom magnetometer.

In an embodiment, the array 104 contains unit cells 106 oriented in all three directions. The array 104 of unit cells 104 can generate of a wider palette of magnetic field patterns, including field profiles with intensity nodes and measurements of the entire vector field pattern at the MIT system 100 surface, and not only the normal component of flux. Each unit cell 106 can include a pattern of conducting lines forming a self-resonant element with a large inductance. The large inductance allows each unit cell 106 to be an efficient source of magnetic flux ($\Phi$=L I), and simultaneously allows each unit cell 106 to be resonant at an anomalously low frequency (much smaller than f0=c/a, where a is the diameter of the unit cell). In an embodiment, each unit cell 106 is configured to operate similar to a resonator such as a magnetic resonator. In some embodiments, the unit cells 106 are configured to act as narrow-band transmitters and receivers, not just as field sources, and can generate narrow band excitations. In other embodiments, the unit cells 106 may be dual-band or multi-band magnetic resonators. For example, the unit cells 106 can be bi-resonant or multi-resonant, enabling additional contrast mechanisms, such as mapping of the real and imaginary parts of conductivity independently.

The unit cells 106 can generate a magnetic field at a plurality of frequencies or range of frequencies. For example, the frequencies of the magnetic field may range from about 1 MHz to about 300 MHz. The unit cells 106 can also sense a magnetic field at a plurality of frequencies or over a range of frequencies. In some embodiments, the plurality of frequencies may be a discrete plurality of frequencies. The plurality of frequencies may correspond to a discrete set of resonance frequencies of the unit cells 106. In some embodiments, the plurality of frequencies may be a continuous spectrum of frequencies.

Smaller dimensions allow the unit cells 106 to be stacked with a much higher number density, which enables high spatial resolution. In some embodiments, the resolution is limited by the spatial density or the dimensions of the unit cells 106. The dimensions of the unit cells 106 may be limited by the width of metal lines of each unit cell 106. In an embodiment, the metal lines are thicker than the skin depth in the metal at a corresponding resonant frequency. The unit cells 106 will be discussed in greater detail with respect to FIGS. 2A-2G.

In some embodiments, the array 104 of unit cells 106 includes excitation unit cells and sensing unit cells. The excitation unit cells may be the same as the sensing unit cells, such as having the same properties and characteristics. In other embodiments, the excitation cells and the sensing cells are different. The excitation unit cells and the sensing unit cells may operate in a transmit/receive mode. For example, the transmit/receive mode may include at least one of a time-division duplex mode or a duplex mode. The duplex mode may be a simultaneous transmit/receive duplex mode using a circular transmit/receive filter or another non-reciprocal transmit/receive filter.

In an embodiment, the MIT system 100 includes a control circuit 108. The control circuit 108 is configured to provide an excitation pattern (e.g., excitation current) to the array of unit cells 104. The excitation pattern can be generated to include any desired magnitude value and any desired phase value. The control circuit 108 can generate multiple excitation patterns with varying excitation currents. In an embodiment, the excitation pattern has an imposed peak value Ip. In one embodiment, each of the unit cells 106 are individually connected to the control circuit 108. The control circuit 108 can be a digital-to-analog converter (DAC) amplifier or an analog-to-digital converter (ADC) amplifier.

In some embodiments, the control circuit may include a processor. The processor may be implemented as a general-purpose processor, an application specific integrated circuit (ASIC), one or more field programmable gate arrays (FPGAs), a digital-signal-processor (DSP), a group of processing components, or other suitable electronic processing components. The control circuit may include memory. The memory can be one or more devices (e.g., RAM, ROM, Flash Memory, hard disk storage, etc.) for storing data and/or computer code for facilitating the various processes described herein. The memory may be or include non-transient volatile memory or non-volatile memory. The memory may include database components, object code components, script components, or any other type of information structure for supporting the various activities and information structures described herein. The memory may be communicably connected to the processor and provide computer code or instructions to the processor for executing the processes described herein.

Now referring to FIGS. 2A-2G, various embodiments of unit cells 206 are illustrated. Each unit cell 206 can be artificially structured electromagnetic unit cell. In an embodiment, the unit cells 206 may include metamaterial unit cells. The unit cells 206 may include a metamaterial cellular architecture. The metamaterial may include a macroscopic composite of a periodic or non-periodic structure, whose function is due to both its cellular architecture and chemical composition. In an embodiment, the unit cells 206 are arbitrarily shaped unit cells. For example, the unit cells 206 may have a square, rectangular, or spherical shape. The unit cells 206 can be structured by artificial inclusions 212, such as conducting lines, with a sub-wavelength size. A wavelength may refer to a distance a radio wave travels during one cycle. In an embodiment, each unit cell 206 includes a pattern of conducting lines. An array of unit cells 206, such as the array 104 illustrated in FIG. 1, can respond to electric and magnetic fields as a homogeneous structure or an effective medium. In an embodiment, the pattern of conducting lines insertions 212 in a unit cell 206 may be specifically designed for dielectric permittivity, magnetic permeability, and index of refraction, and placed at a desired location in the unit cell. In an embodiment, the unit cells 206 may be resonant or non-resonant.

The insertions 212 may be formed in a variety of patterns on the unit cells 206. For example, FIG. 2A illustrates a unit cell 206A with concentric split rings insertion 212A. FIG. 2B illustrates a unit cell 206B with a split ring insertion 212B having shoulders at the split. FIG. 2C illustrates a unit cell 206C with concentric box split rings 212C insertion. FIG. 2D illustrates a unit cell 206D with a conical helix insertion 212D. FIG. 2E illustrates a unit cell 206E with an interleaved "L" rings insertion 212E. FIG. 2F illustrates a unit cell 206F with an "I" inclusion 212F with broad shoulders. FIG. 2G illustrates a unit cell 206G with an opposing box split rings insertion 212G. The selection of an inclusion 212 for the unit cells 206 may be made by those skilled in the art responsive to the particular design requirements and materials available. Another example of inclusions 212 in unit cells 206 may include multi-turn rectangular planar spiral, or several such spirals lying in different planes and connected by conducting vias. When more than two such planar spirals are connected, they may be described as a "three-dimensional meander line." An illustration of coupled, multi-turn rectangular planar spiral inserts may be drawn from superconducting quantum interference (SQUID) antenna implementations and inductive-coupling RFID tags.

In an embodiment, the artificially structured electromagnetic unit cells 206 can include at least two periodically arranged, artificially structured electromagnetic unit cells. In an embodiment, the artificially structured electromagnetic unit cells 206 can include at least two artificially structured sub-wavelength electromagnetic unit cells. In an embodiment, the artificially structured electromagnetic unit cells 206 can respectively include a split ring resonator insertion optimized to generate a high inductance density. For example, see the split ring 212B of FIG. 2B. In an embodiment, the artificially structured electromagnetic unit cells 206 can respectively include two orthogonally oriented split ring resonator insertions optimized to generate a high inductance density. In an embodiment, the artificially structured electromagnetic unit cells 206 can respectively include three orthogonally oriented split ring resonator insertions optimized to generate a high inductance density. In an embodiment, the artificially structured electromagnetic unit cells 206 can respectively include a spiral insertion optimized to generate a high inductance density. The spiral insertion can include a rectangular or circular spiral insertion optimized to generate a high inductance density. In an embodiment, a unit cell 206 of the artificially structured electromagnetic unit cells 206 can include a conical helix or cylindrical helix insertion optimized to generate a high inductance density. For example, see the conical helix insertion 212D of FIG. 2D. In an embodiment, a unit cell 206 of the artificially structured electromagnetic unit cells 206 can include two orthogonally oriented conical helical insertions optimized to generate a high inductance density. In an embodiment, a unit cell 206 of the artificially structured electromagnetic unit cells 206 can include three orthogonally oriented cylindrical helical insertions optimized to generate a high inductance density. In an embodiment, a unit cell 206 of the artificially structured electromagnetic unit cells 206 includes a pyramidal helical insertion optimized to generate a high inductance density. In an embodiment, the artificially structured electromagnetic unit cells 206 are configured to induce a B1 magnetic field component orthogonal to the z-axis. In an embodiment, the artificially structured electromagnetic unit cells 206 are configured to induce a first B1 magnetic field component orthogonal to the z-axis and a second B1 magnetic field component orthogonal to the first B1 magnetic field component. In an embodiment, the artificially structured electromagnetic unit cells 206 are configured to induce magnetic field B1 components in all three mutually orthogonal orientations.

In an embodiment, the artificially structured electromagnetic unit cells 206 may include a sub-wavelength arrangement of magnetic dipole unit cells. For example, the sub-wavelength arrangement may include unit cells 206 having cellular dimensions of less than one-half of a wavelength. For example, the sub-wavelength arrangement may include unit cells having cellular dimensions of less than one-quarter of a wavelength. For example, the sub-wavelength arrangement may include a deeply sub-wavelength arrangement. For example, the sub-wavelength arrangement may include unit cells 206 having cellular dimensions of less than one-tenth of a wavelength. In an embodiment, the unit cells 206 are densely packed to deliver a relatively large magnetic field or a large magnetic flux. In an embodiment, the artificially structured electromagnetic unit cells 206 include a sub-wavelength arrangement of magnetic multipole unit cells. In an embodiment, the artificially structured electromagnetic unit cells 206 include a deeply sub-wavelength arrangement of magnetic multipole unit cells.

In an embodiment, each unit cell 206 can be configured to generate a magnetic field $B_1$ in the near-field region. As used herein, B may generally be used a symbol for a radio frequency field strength. In an embodiment, the at least two unit cells 206 can be configured to generate a pulse of a tunable radiofrequency magnetic field $B_1$. In an embodiment, the tunable radiofrequency magnetic field $B_1$ includes a frequency, amplitude, or polarization tunable radiofrequency magnetic field $B_1$. In an embodiment, the tunable radiofrequency magnetic field $B_1$ is tunable over a portion of the 1-300 MHz range. This frequency range can be used for magnetic resonance imaging (MRI), including nuclear magnetic resonance (NMR) imaging and electron paramagnetic resonance (EPR) imaging, or magnetic induction tomography (MIT). In an embodiment, there is no true lower bound on the frequency range. In an embodiment, resonant unit cells 206 producing the magnetic field B are loaded with additional capacitors in order to lower the resulting resonance frequency below their natural, unloaded resonance frequency. In another embodiment, the frequency of the excitation field is so low, or even precisely zero (DC), that the apparatus senses mostly the induced magnetization, rather than electric currents, and the image contrast is based predominantly on magnetic susceptibility rather than electric conductivity. The upper frequency limit for the $B_1$ frequency results from high-frequency wave attenuation and electric field absorption in the body. Reducing total electric field absorption in the body allows use of higher radiofrequency magnetic fields B1, enabling higher detection efficiency.

In an embodiment, an array of unit cells is configured to be coaxially disposed about the z-axis. The z-axis may refer to a longitudinal axis relative to a bore of the MIT system. In an embodiment, the array of unit cells 104 includes an arcuate shape dimensioned to be mounted or positioned within at least a portion of the bore of a MIT system. In an embodiment, the arcuate shape is dimensioned to be mounted or positioned around less than 180-degrees of the circumference of the bore. In an embodiment, the arcuate shape enables the array 104 to be mounted or positioned around 180-degrees or more of the circumference of the bore. In an embodiment, the shape enables the array 104 to be mounted or positioned around less than 270-degrees of the circumference of the bore. In an embodiment, the array of unit cells 104 may have a cylindrical or an annular shape dimensioned to be mounted or positioned within the bore of the MIT system. In an embodiment, the array of unit cells 104 includes two arcuate shaped portions; each dimensioned to be less than 180-degrees of the circumference of the bore, and mounted or positioned facing each other across the z-axis. In an embodiment, the array of unit cells 104 includes two generally planar portions, each configured to be mounted or positioned facing the other across the z-axis.

In an embodiment, the artificially structured electromagnetic unit cells 206 are configured to generate a highly inductive electromagnetic near field. In an embodiment, the artificially structured electromagnetic unit cells 206 are configured to generate a magnetic field-dominant radiofrequency near-field whose magnetic ($B_1$) and electric ($E_1$) field intensities are such that ($B_1$c)/$E_1$>1 (where "c" is the speed of light). In an embodiment, the artificially structured electromagnetic unit cells 206 are configured to generate a magnetic field-dominant radiofrequency near-field where ($B_1$·c)/$E_1$>10. For example, this is equivalent to ($H_1$·$Z_0$)/$E_1$>10 (where $H_1$ is a component of the magnetic field and where $Z_0$ is the free-space impedance). In an embodiment, the artificially structured electromagnetic unit cells are configured to generate a magnetic field $B_1$ that includes a gradient orientated transverse to the z-axis. In an embodiment, the artificially structured electromagnetic unit cells 206 are configured to generate a magnetic field B1 that includes two orthogonal gradients orientated transverse to the z-axis. In an embodiment, the pulse of radiofrequency magnetic field $B_1$ is linearly polarized relative to the z-axis. In an embodiment, the pulse of radiofrequency magnetic field $B_1$ is circularly polarized relative to the z-axis.

Figure 3A:
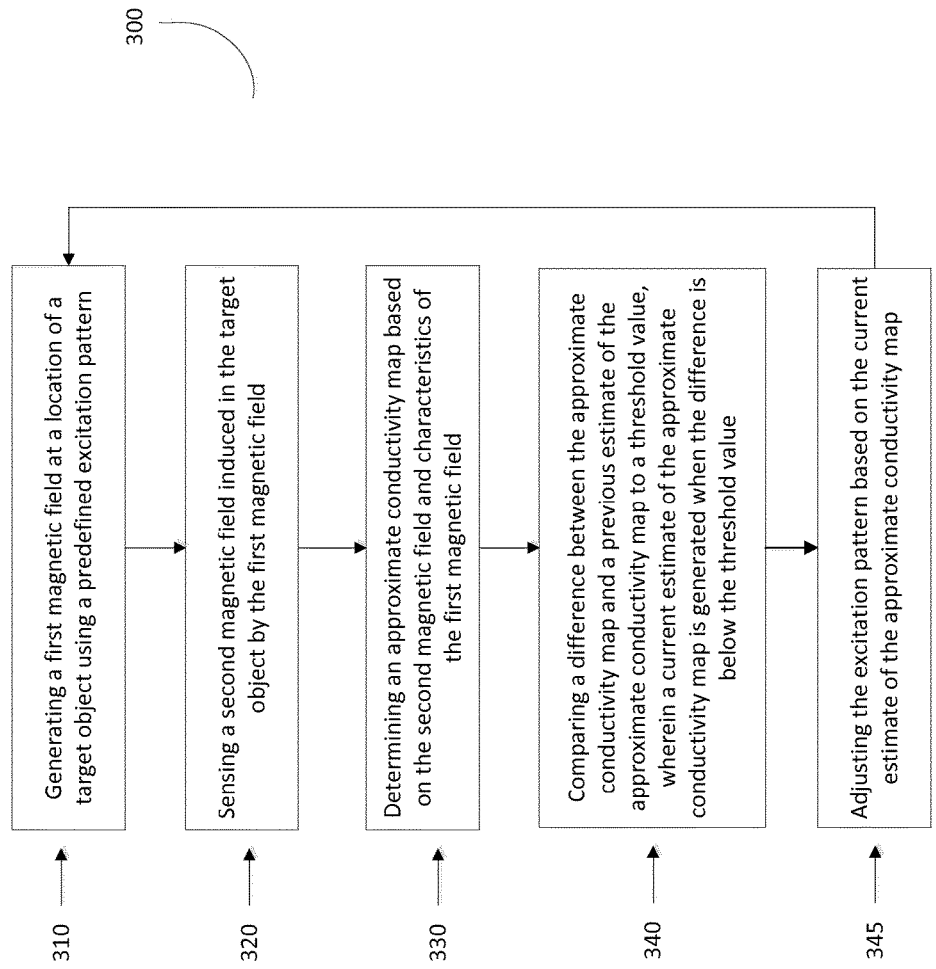
FIG. 3A is a flow diagram of a first method for performing magnetic induction tomography imaging of an object, according to one embodiment.

Now referring to FIG. 3A, a flow diagram of a method 300 for imaging an object in accordance with an illustrative embodiment is depicted. In brief overview, the method 300 includes an array of unit cells generating a first magnetic field using an excitation pattern in the direction of a target object (310) and sensing a second magnetic field induced in the target object by the first magnetic field (320). The method further includes a control circuit determining an approximate conductivity map based on a minimum of the first magnetic field (330). The minimum may correspond to a higher conductivity region of the target object. The method further includes adjusting the excitation pattern based on a previous estimate of the approximate conductivity map (340). The method further includes comparing a difference between the approximate conductivity map and the previous estimate of the approximate conductivity map to a threshold value (345).

In an embodiment, the method 300 includes an array of unit cells generating a first magnetic field using an excitation pattern in the direction of a target object (310). The method 300 is directed to imaging the target object to obtain high dynamic range, high resolution maps of conductivity for the target object. An MIT system can generate a magnetic field with a predefined magnitude, direction, and phase and excite a large array of elements simultaneously, which can lead to enhanced dynamic range and improved spatial resolution of a reconstructed image of the object. In an embodiment, the optimal distribution of excitation magnitudes and phases for the subsequent image frame can be calculated using a mathematical algorithm based on the knowledge of a transmission matrix measured during the acquisition of the previous image frame, and any prior knowledge about the scene or object being imaged.

In some embodiments, prior to generating the first magnetic field, the control circuit may determine a first excitation pattern for imaging the target object. To determine an excitation pattern, a trial field pattern may be used and activated. For example, a trial field pattern (e.g., the first excitation pattern) may be used when the excitation pattern is provided to the array of unit cells to image the target object for the first time. In an embodiment, the optimal distribution of excitation magnitudes and phases for the subsequent image frame can be calculated using a mathematical algorithm based on the knowledge of a transmission matrix measured during the acquisition of the previous image frame, and any prior knowledge about the scene or object being imaged. The transmission matrix may be described by the following equation:

$$\Phi_i = \Sigma_{j=1}^{N_t} T_{ij} I_j, \quad i=1 \ldots N_r \tag{Eq. 1}$$

where $\Phi_i$ is the magnetic flux (directly proportional to the emf) as measured by the i-th receive element of the MIT system, and $I_j$ is the current in the j-th transmit element of the MIT system. Here, $N_t$ is the number of transmit elements, and $N_r$ is the number of receive elements. In a first approximation, where currents induced by secondary magnetic fields are neglected, one may express the transmission matrix in terms of the (quasistatic) field propagators by the following equation:

$$T_{ij} = \Sigma_{k=1}^{K} \vec{n}_i \vec{G}_2(\vec{x}_i; \vec{x}_k) \sigma_k \vec{G}_1(\vec{x}_k; \vec{x}_j) \vec{n}_j = \Sigma_{k=1}^{K} S_{ijk} \sigma_k \tag{Eq. 2}$$

where K is the number of voxels used in the current iteration of the algorithm (see below for the description of how this number is decided), $\sigma_k$ is the spatially averaged conductivity in a voxel centered at $\vec{x}_k$ and $\vec{G}_{1,2}$ are the tensor (dyadic) Green's functions of the source and the induced currents in the voxel, respectively. The unit vectors $\vec{n}_{i,j}$ take into account the orientation of the receive and transmit elements of the MIT system, respectively. Any necessary constants of proportionality can be absorbed into the definitions of $\vec{G}_{1,2}$. The voxels can be hexahedral, tetrahedral or prismatic elements. The number of voxels, their dimensions and positions can change dynamically during the an acquisition sequence. For example, an initial scan of an object may begin with a small number of voxels, whose average conductivities are first crudely estimated, and then proceed with an increasing number of voxels as more data is collected.

In Eq. 2, the voxel conductivities should be understood as deviations of the actual conductivity from a certain predefined map. For example, a predefined map may be a map using a previously taken image of the same object, or selected from a library of images of similar objects belonging to the same class, such as a library of human body images. In an embodiment, if these deviations are determined to be larger than a certain tolerance (e.g., threshold value), the map is updated by adding these deviations to it, and another iteration of the method 300 can be performed. The next iteration of the method 300 may be performed with the propagators $\vec{G}_1(\vec{x}_k; \vec{x}_j)$ calculated using an updated conductivity map, as will be described in greater detail below.

In an embodiment, the response of an object to an excitation pattern can be measured using a sensitivity matrix. The sensitivity matrix, $M_{jk}$ can be defined by the following equation:

$$\Phi_i = \sum_{k=1}^{K} M_{ik}\sigma_k \quad \text{(Eq. 3)}$$

As indicated in the Eq. 3, the sensitivity matrix M can depend on the choice of voxels. In an embodiment, the sensitivity matrix M depends on the excitation pattern $\vec{I} = \{I_j\}$, as can be seen from the combination of Eq. 2 and Eq. 3:

$$M_{ik} = \sum_{j=1}^{N_t} S_{ijk} I_j \quad \text{(Eq. 4)}$$

Consequently, sensitivity with respect to the conductivities can be adjusted by choosing an appropriate illumination pattern. For example, sensitivity can be deliberately increased in a certain region of interest, or it can be increased in regions of estimated low conductivity, such as to decrease the relative error in the determination of conductivities in low-conductivity regions. In what follows, the notion of local sensitivity of a given voxel k is used, defined as the norm of vector $\vec{M}^{(k)} = \{M_{ik}\}$, where the index i runs over all values of the k-th column of the sensitivity matrix M.

As stated above, a trial field pattern may be used to determine an initial excitation pattern. In the array of unit cells, each unit cell may be configured to operate as a transmit element and a receive (e.g., sensing) element. The trial field pattern may utilize all of the transmit unit cells at the same time (simultaneously) or according to a pre-determined order based on a desired field pattern. The trail field pattern provides a magnetic field to an object and a resulting magnetic flux is measured (sensed) by all of the receive unit cells. In some embodiments, the array of unit cells can generate a first magnetic field at a plurality of frequencies and can sense a second magnetic field at a plurality of frequencies. The plurality of frequencies may be a discrete plurality of frequencies. For example, the plurality of frequencies may correspond to a discrete set of resonance frequencies of the unit cells. In some embodiments, the plurality of frequencies may be a continuous spectrum of frequencies. The generated magnetic field may range from about 1 MHz to about 300 MHz. 300 MHz may be the highest frequency at which there is still substantial penetration through the thickness of an object, for example through the thickness of the human body. In an embodiment, the frequency range of about 1 MHz to about 300 MHz is selected to provide a full range of medical and security imaging applications. In general, a frequency may be selected at which a penetration depth through the thickness of the object exceeds at least, about 20 cm. The magnetic field can be an alternating (AC) magnetic field.

The excitation pattern used to generate the magnetic field can be defined by the vector Ij, also referred to as a trial vector or excitation current. The trial vector can be generated randomly, or it may utilize any prior knowledge about the scene. For example, the trail vector and trial field pattern can be determined or calculated based on previous measurements, including at least one of a previously taken image of the object or an image selected from a library of images of similar objects. In one embodiment, when a magnetic induction tomography system is used to image a body part, prior knowledge may include imaging data obtained previously for the same or for a sufficiently similar body part. In other embodiments, the trial vector and the trial field pattern are calculated based on randomly selected values.

Once the first excitation pattern is determined, the control circuit may excite the array of unit cells with the first excitation pattern. Each unit cell may be activated simultaneously using the first excitation pattern. In other embodiments, the individual unit cells in the array may be activated at different times or in combinations together based on a pre-determined order using the excitation pattern. Each unit cell in the array of unit cells may be activated with a different but non-vanishing amplitude. For example, in one embodiment, all unit cells can be excited simultaneously, with different but non-vanishing amplitudes, creating the field distribution most preferred for imaging the given conductivity map.

The array of unit cells can be configured to generate a magnetic field based on a predetermined magnitude, direction, and phase. The magnetic field can be generated such that it is perpendicular to a plane of the array of unit cells. The array of unit cells can include a first set of unit cells that generate a first magnetic field and a second set of unit cells that sense a second magnetic field. In some embodiments, the array of unit cells includes two layers of unit cells, where a first layer of unit cells is stacked on top of a second layer of unit cells. The first layer of unit cells can generate a first portion of the first magnetic field perpendicular to a plane of the array of unit cells and the second layer of unit cells can generate a second portion of the first magnetic field orthogonal to a plane of the array of unit cells. In some embodiments, the array of unit cells includes three or more layers of unit cells. In one embodiment, each layer of the three or more layers of unit cells can generate a portion of the first magnetic field. The array of unit cells may be formed into a planar formation, a curved formation, or a random formation.

The excitation pattern can be provided in a pulsed excitation pattern. For example, the excitation pattern may be used for (magnetic induction) relaxation tomography. In relaxation tomography, an object can be exciting with a very short pulse (<1 ns) and then the response may be measured two or more times while the induced currents are still decaying. The measurements may be performed over a pre-determined time window based on the target object being imaged or measured. Using the measured response, the control circuit can derive the complex dielectric constant map, with real and imaginary parts. In some embodiments, a first magnetic field can be generated at a first time "t" and a second magnetic field can be sensed at a second time "t+Δt." For example, in magnetic relaxation tomography, a target object may be subjected to a first magnetic field and the response or second magnetic field induced in the target object may be measured one or more times. The array of unit cells may sense the second magnetic field two or more times after the excitation pattern is turned off. In some embodiments, the array of unit cells may measure currents induced in the target object as the currents are decaying.

In an embodiment, the method includes sensing or measuring, by the array of unit cells, a second magnetic field induced in the target object by the first magnetic field (step 320). The second magnetic field can be a response by the object to the first magnetic field. For example, the second magnetic field may be a magnetic flux or an amount of magnetic field passing through a given surface of the object. In some embodiments, the response by the object may depend on the frequency of the applied magnetic field. The array of unit cells can be sensitive to gradients of the magnetic field (e.g., gradiometers). In some embodiments, the array of unit cells can measure a gradient of three components of the second magnetic field.

In an embodiment, the measurements can be done over a range or plurality of frequencies. The array of unit cells can sense a plurality of magnetic fields induced in a target object by initial magnetic fields. For example, the measured response can be a permittivity measurement (e.g., complex permittivity) indicating how much resistance is encountered when the magnetic field was applied to the object. In general, permittivity is not a constant, as it can vary with the position in the medium, the frequency of the magnetic field applied, as well as other parameters such as humidity and temperature. In a nonlinear medium, the permittivity can depend on the strength of the magnetic field. Permittivity as a function of frequency can take on real or complex values.

To measure the complex permittivity, the array of unit cells may be broadband unit cells (e.g., non-resonant unit cells) that can measure the response over a range of frequencies. In other embodiments, the array of unit cells may include dual-band or multi-band magnetic resonators. For example, two or more narrow-band excitations can be applied to the object using dual-band or multi-band magnetic resonators. In some embodiments, hyperspectral imaging is performed, in which measurements are performed across a desired electromagnetic spectrum. In an embodiment, the contrast of MIT images in biological tissues is almost entirely due to the (complex) electrical conductivity. At such low frequencies, complex conductivity, $\sigma_c = \sigma + i\omega \in_r$, is predominantly real in live tissues, although its phase may vary significantly in other substances, such as rocks and soils. Multi-frequency, with several discrete excitation frequencies, or hyperspectral (e.g., broad-spectrum) version of MIT can provide a second contrast mechanism by mapping both the real and imaginary parts or, equivalently, the magnitude and phase of complex conductivity. In geophysical applications, magnetic susceptibility of the medium can be non-negligible due to presence of iron and other magnetic elements, which enables additional contrast mechanisms. In an embodiment, a real dielectric constant can be obtained and used to discern non-conducting materials whose real dielectric constants are different.

In some embodiments, the array of unit cells may be referred to as sensing units. For example, the array of unit cells may include excitation unit cells and sensing sell units. The excitation unit cells may be the same as the sensing unit cells. In other embodiments, the excitation unit cells are different from the sensing unit cells. The sensing units may be insensitive to magnetic fields produced directly by the excitation unit cells. The sensing units may be sensitive to magnetic fields produced by eddy currents in the target object being imaged.

The method further includes determining an approximate conductivity map based on a minimum of the first magnetic field (330). The minimum may correspond to a higher conductivity region of the target object. The minimum may be an intensity null. In some embodiments, the minimum is one of a local minimum or a global minimum. In some embodiments, the minimum is one of a plurality of minima corresponding to a plurality of estimated conductivity maxima.

In some embodiments, to determine the minimum the control circuit determines a magnetic flux value for the target object based on the second magnetic field. The magnetic flux value can be based on a response of the sensitivity matrix to the first excitation pattern. As stated above with respect to equation 1, the magnetic flux ($\Phi_i$) can be directly proportional to the emf, as measured by the i-th receive element of the MIT system, and $I_j$ is the current in the j-th transmit element of the MIT system.

In an embodiment, the control circuit generates a conductivity map (i.e., approximate conductivity map) based on the determined magnetic flux and estimated values as described above. Analyzing the measured results, there can be $M \le N_r$ measured complex numbers, $\Phi_i$, and K complex-valued unknowns, $\sigma_k$. In one embodiment, the phase of $\sigma_k$ is presumed to be to known, for example, presumed to be zero. Therefore, there are K real-valued unknowns to be estimated.

However, unlike M, K is not fixed by the geometry of the MIT system and can be chosen to maximize the accuracy or reliability of the estimate, as the sensitivity matrix depends on the choice of voxels. To select values for K, several initial estimates of a conductivity map can be obtained using a method 370, as illustrated in FIG. 3B.

Figure 3B:
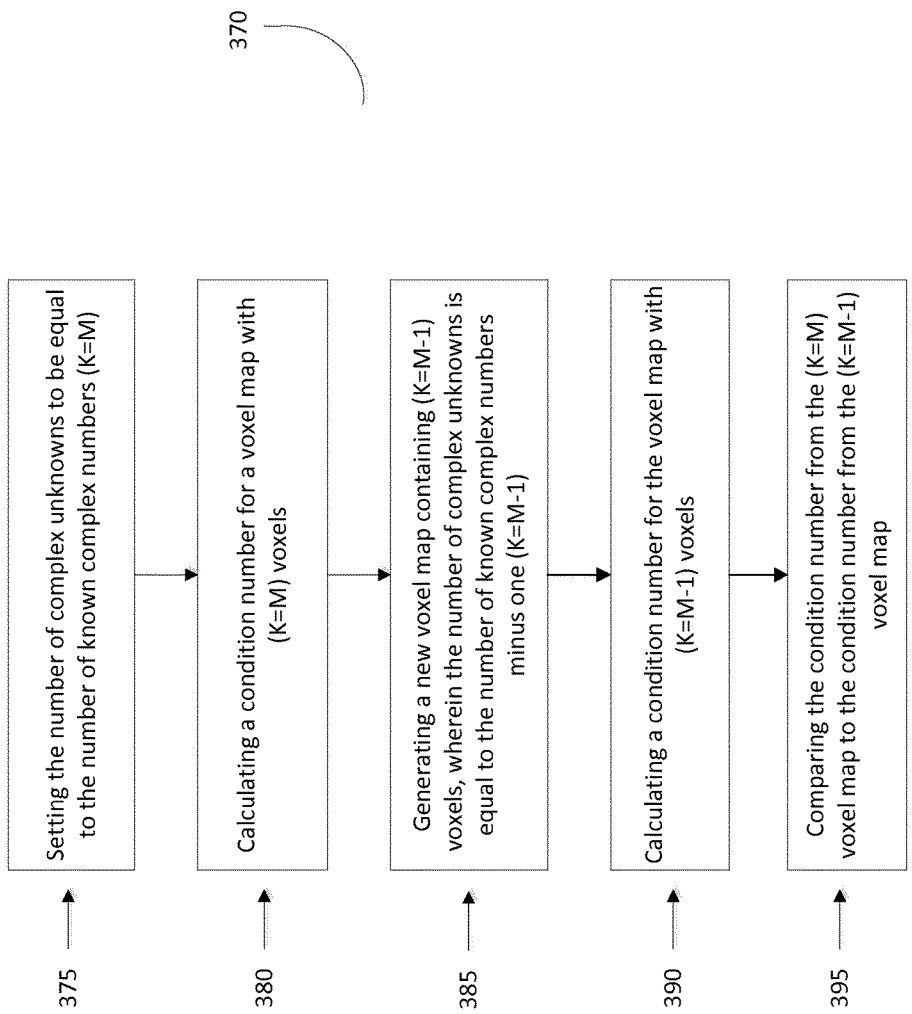
FIG. 3B is a flow diagram of a method for determining estimates for a conductivity map (Step 330 in FIG. 3A), according to one embodiment.

In more detail, FIG. 3B depicts a flow diagram of a method 370 for determining estimates for a conductivity map, according to one embodiment. In an embodiment, method 370 is a sub-method of method 300 and the values determined can be implemented to perform magnetic induction tomography of a target object as described by method 300. First, (step 375) the number of unknowns can be set to be equal to the number of known complex numbers, for example assuming K=M. Using K=M, an exact solution to the linear algebra problem of size M-by-M is obtained, and stored. A condition number for a voxel map with K=M voxels can be calculated (Step 380). The condition number of this linear problem, i.e. the condition number of the sensitivity matrix M, is also stored. This information may be stored on a database coupled to the control circuit. In some embodiments, the database is communicatively coupled to the control circuit, for example, via a wired or wireless connection.

Next, the number of complex unknowns can be set to be equal to the number of known complex numbers minus one (K=M−1) and a new voxel map with K=M−1 voxels is generated (step 385). In one embodiment, the new voxel map with K=M−1 voxels is obtained from the old voxel map, by removing one voxel. In another embodiment, the new map is obtained from the old map by merging two voxels into one. Using K=M−1, a least-squares best-fit solution to the over determined problem with M knowns and K unknowns can be obtained by virtue of the singular value decomposition of a measurement sensitivity matrix (known as Moore-Penrose pseudoinverse). A condition number for the voxel map with K=M−1 voxels is then calculated (Step 390). The condition number from step 380 is then compared with the condition number from step 390 (Step 395). For example, if the condition number of the singular value decomposition, calculated during step 390, is smaller than the condition number of step 380, the results of step 390 are used instead of the output of step 380, as a better estimate of the conductivity map on a somewhat reduced-resolution voxel grid. In other words, the conductivity values for these K=M−1 are updated with the new values obtained from the reduced-size matrix. In one embodiment, to determine the voxel to be removed or merged, either the lowest estimated conductivity or the lowest local sensitivity voxel can be selected. In another embodiment, a trial voxel is removed or merged with its neighbor, and the algorithm scans through a set of low-conductivity voxels, removing one at a time and determining the resulting condition number of the reduced-size matrix. The inverse of the condition number may be referred to as a voxel map quality score, or voxel score for brevity. In some embodiments, a larger condition number may indicate a bad or worse score than a lower condition number and an inverse of the condition number can be used as the score. The control circuit can determine a voxel score for the conductivity map. The voxel score indicates the accuracy of the conductivity map determination for a given voxel map.

If the results from step 390 are used instead of the results from step 380, the method 370 can repeat the above described process, but with K=M−2. In an embodiment, the iterations stop when the condition number increases relative to the previous step. For example, in some embodiments, the voxel score is compared to a threshold value. The threshold value may be a result from a previous calculation or it may be an assigned value. If the voxel score is greater than the threshold value, the conductivity map is updated with the information available for these new K=M−2 voxels. When the conductivity map is updated, the update may include changing a number of voxels in the conductivity map, changing dimensions of at least one voxel in the conductivity map, or changing a position of at least one voxel in the conductivity map. If the voxel conductivity score is equal to or less than the threshold value, the conductivity map is not updated. The current conductivity map is considered a final conductivity map and is output. For example, iterations may stop at step 390, in which case only the estimates obtained in step 380 are kept as meaningful.

Referring back to FIG. 3A, in an embodiment, the method further includes the control circuit adjusting the excitation pattern based on a previous estimate of the approximate conductivity map (340). The control circuit can determine a new or second excitation pattern for imaging the object based on the response of the sensitivity matrix to the first excitation pattern and historical data related to the object. In an embodiment, the sensitivity matrix can be used to indicate a local sensitivity of the object to the applied magnetic field. Based on the measured response, the second or any subsequent excitation pattern can apply an excitation whose local field strength in voxel k is inversely proportional to the local sensitivity of the voxel k in the previous measurement. In another embodiment, this local field strength is inversely proportional to the conductivity of voxel k. Consequently, the excitation pattern can be configured to provide a magnetic field to an area with high conductivity that is a different intensity than a magnetic field applied to an area with a low conductivity.

In an embodiment, the new or second excitation pattern may be described by the complex-value pattern of currents $I_j = I_j^{(2)}$. The change of vector I modifies the measurement sensitivity and the condition number of the sensitivity matrix M, because of equations 3-4. The use of varying excitation patterns can provide an image with dynamic range and greater spatial resolution in objects with highly inhomogeneous, high-contrast distributions of conductivity.

In an embodiment, the vector I is now chosen such as to minimize the condition number of measurement sensitivity matrix M, assuming that the three-dimensional conductivity map is the one estimated and as described above. A physical manifestation of this choice is typically the production of a magnetic field pattern that has a null or at least a minimum of magnetic field intensity on the highest-conductivity voxel. Another manifestation may be an increase in magnetic field intensity in low-conductivity regions. As a result of this choice, a higher signal-to-noise ratio, and consequently smaller relative error in the determination of conductivity, is obtained for voxels with relatively low conductivity. For example, in one embodiment, the array of unit cells can provide a magnetic field that directs an approximate null of the magnetic field at the location corresponding to the highest conductivity value (the brightest spot in the conductivity image). In some embodiments, the array of unit cells can provide a magnetic field with more than one null, each null directed at different portions of the object to be imaged. For example, if the image indicates several areas of high conductivity, (e.g., several bright spots in the image) each location can approximately nulled simultaneously.

The control circuit can provide the second excitation pattern to the array of unit cells. Upon receiving the second excitation pattern, the array of unit cells can generate a new magnetic field (e.g., third magnetic field) in the direction of the object and measure a response (e.g., fourth magnetic field) of the object to the second excitation pattern. The third magnetic field may apply a different field strength to different locations on the object based on determined voxel values. For example, the third magnetic field may direct a greater magnetic field at points in the image with low voxel values and a lower magnetic field at points in the image with high voxel values. In some embodiments, the third magnetic field generates a null magnetic field at a location on the object with a highest conductivity voxel value. The third magnetic field may generate a null magnetic field at one or more locations on the object that have a highest conductivity voxel value.

The response, $\Phi_i^{(2)}$, of the object to the second excitation pattern (e.g., third magnetic field) using the second excitation current $I_j^{(2)}$ can be measured and used to determine a new estimate of a conductivity map, for example using method 300 as described above. For example, following the same steps as described above, the control unit can determine a new (e.g., second magnetic flux value) magnetic flux value for the object based on the measured response. The control unit may then update the conductivity map based on the second magnetic flux value.

In an embodiment, the control circuit may combine the first magnetic flux value and the second magnetic flux value to create a test conductivity map. For example, in some embodiments, the measurements can be combined to analyze a 2M-by-K problem with 2M knowns and K unknowns using the same iterative process described above with respect to FIG. 4A. The control circuit may compare a difference between the approximate conductivity map and a previous estimate of the approximate conductivity map to a threshold value (345). For example, the control circuit may compare the updated or most recent conductivity map to the test conductivity map and update the conductivity map based on the comparison if the difference is above the threshold value. The threshold value may refer to an image quality tolerance level. In some embodiments, the threshold value may be set at 1%. In one embodiment, the resulting two conductivity maps, the conductivity map generated using the first magnetic flux value and the conductivity map using the second magnetic flux value, can be compared to determine which conductivity map is a better or more accurate conductivity map. In an embodiment, the better conductivity map is selected using one or more criteria including, the condition number of the singular value decomposition, or the spatial resolution obtained. The result of the comparison and selection may be identified as a final conductivity map.

In an embodiment, the control circuit can determine an optimum excitation current based on the updated conductivity map, the first magnetic flux value, and the second magnetic flux value. For example, the final conductivity map can be used to determine the optimum excitation vector, $I_j^{(3)}$. Third excitation pattern can be generated based on the optimum excitation vector, $I_j^{(3)}$ and provided to the object. The array of unit cells senses and measures the response of the object t of the third excitation pattern. The measurements are collected and analyzed first separately and then in combination with the data from all previous steps, 1-2.

The method 300 as described here may continue until a desired spatial resolution (e.g., threshold value) is obtained. The number of times the object or a region of interest is illuminated and sensed can be larger or smaller than the number of individually controlled unit cells (e.g., resonant elements). The sequence can be terminated as soon as a certain level of confidence in the image reconstruction is obtained, or when the target spatial resolution is reached. In some embodiments, the number of iterations in this process can exceed the number of independent excitations (N). This is because the different excitation vectors $I_j^{(n)}$ do not necessarily form the full linear basis after the iteration count, n, reaches N. The linear dependency of the "new" excitation vector with the set of all previous excitation vectors does not preclude the possibility of obtaining a better measurement than in all the previous iterations, considering the variable levels of noise in the system. For example, the presence of a finite noise floor can make two linearly dependent vectors or sets of vectors non-equivalent from the measurement perspective.

Figure 4:
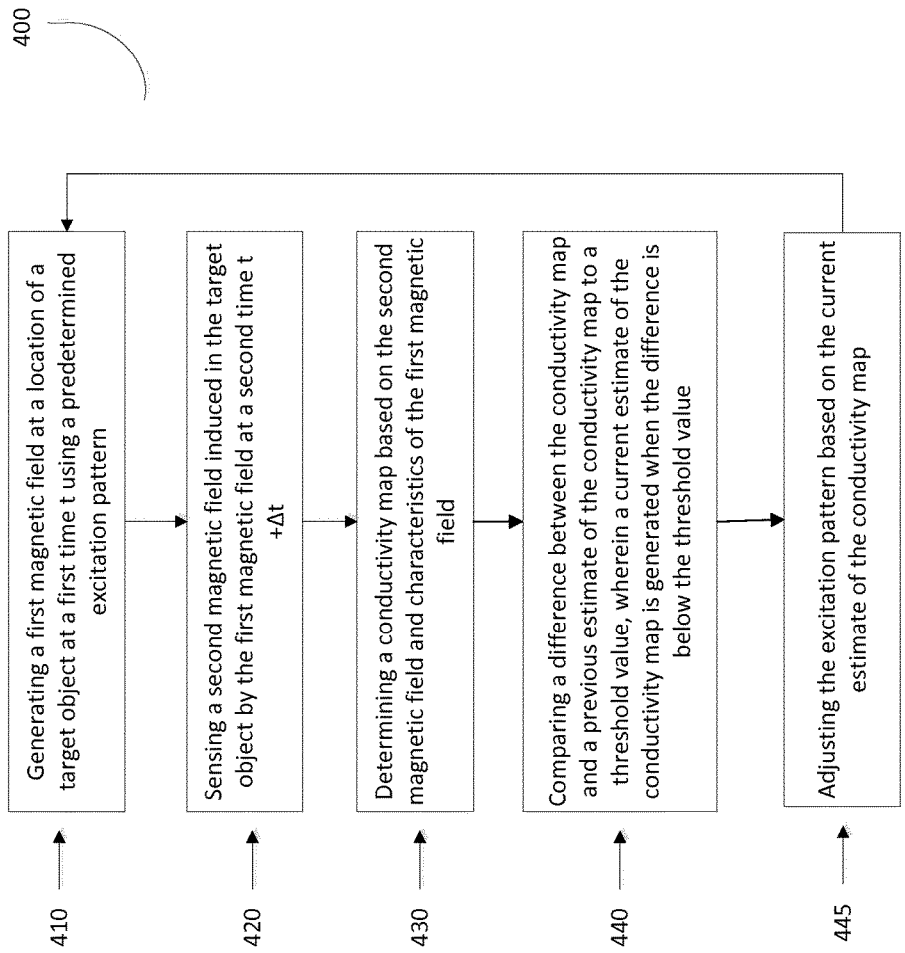
FIG. 4 is a flow diagram of a second method for performing magnetic induction tomography imaging of an object, according to one embodiment.

FIG. 4 depicts a flow diagram of a method 400 for imaging a target object. The method includes an array of unit cells generating a first magnetic field using an excitation pattern in the direction of a target object at a first time t (410). In some embodiments, such as in relaxation tomography, the measurements may be performed over a pre-determined time window based on the target object being imaged or measured. For example, the excitation pattern can be provided in a pulsed excitation pattern. In relaxation tomography, an object can be excited with a very short pulse (<1 ns).

In an embodiment, the method includes sensing a second magnetic field induced in the target object by the first magnetic field at a second time t+Δt (420). The array of unit cells can sense the second magnetic field or gradients one or more times while induced eddy current in the target object are decaying. The array of unit cells may sense the second magnetic field or gradients two or more times after the excitation pattern is turned off. The measurements may be continued until the induced eddy currents are gone or may continue for a pre-determined time window.

The method further includes a control circuit determining a conductivity map based on a minimum of the first magnetic field (430). The minimum may correspond to a higher conductivity region of the target object. Using the measured response, the control circuit can derive a complex dielectric constant map, with real and imaginary parts. The method further includes the control circuit adjusting the excitation pattern based on a previous estimate of the conductivity map (440). In some embodiments, the excitation pattern is adjusted to generate a minimum magnetic field at a higher conductivity region of the target object. The method further includes comparing a difference between the conductivity map and the previous estimate of the conductivity map to a threshold value (445). For example, and similar to the methods described above with respect to method 300, method 400 may continue until a desired spatial resolution (e.g., threshold value) is obtained. The sequence can be terminated as soon as a certain level of confidence in the image reconstruction is obtained, or when the target spatial resolution is reached.

Figure 5:
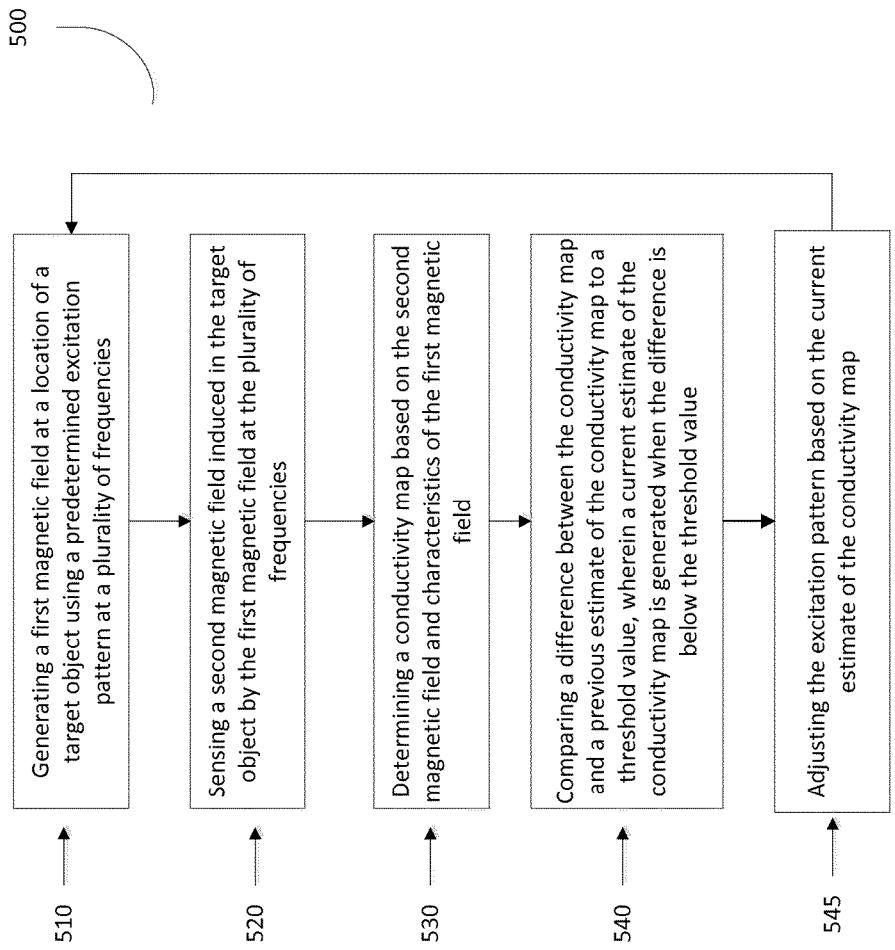
FIG. 5 is a flow diagram of a third method for performing magnetic induction tomography imaging of an object, according to one embodiment.

FIG. 5 depicts a flow diagram of a method 500 for imaging a target object. In brief overview, the method includes an array of unit cells generating a first magnetic field using an excitation pattern in the direction of a target object at a plurality of frequencies (510) and sensing a second magnetic field induced in the target object by the first magnetic field at the plurality of frequencies (520). The method further includes a control circuit determining a minimum of the first magnetic field (530). The minimum may correspond to a higher conductivity region of the target object. The method further includes adjusting the excitation pattern based on the higher conductivity region of the target object (540). The method further includes comparing a difference between the conductivity map and the previous estimate of the conductivity map to a threshold value (545).

In an embodiment, the array of unit cells can generate a first magnetic field using an excitation pattern in the direction of a target object at a plurality of frequencies (510). For example, to perform complex permittivity, the measurements can be done over a range or plurality of frequencies. The measured response can be a permittivity measurement (e.g., complex permittivity) indicating how much resistance is encountered when the magnetic field was applied to the object. In general, permittivity is not a constant, as it can vary with the position in the medium, the frequency of the magnetic field applied, as well as other parameters such as humidity and temperature. In a nonlinear medium, the permittivity can depend on the strength of the magnetic field. Permittivity as a function of frequency can take on real or complex values. The frequencies of the magnetic field may range from about 1 MHz to about 300 MHz. The 300 MHz may correspond to a highest frequency at which there is still penetration through a thickness of the object (e.g., human body or skin). In some embodiments, the array of unit cells can generate a magnetic field at a frequency in which a penetration depth of the magnetic field though the object exceeds 20 cm. The plurality of frequencies may correspond to a discrete set of resonance frequencies of the unit cells. In some embodiments, the plurality of frequencies may be a continuous spectrum of frequencies.

In an embodiment, the array of unit cells can sense a second magnetic field induced in the target object by the first magnetic field at the plurality of frequencies (520). To measure the complex permittivity over a plurality of frequencies, the array of unit cells may be broadband unit cells (e.g., non-resonant unit cells) that can measure the response over a range of frequencies. In other embodiments, the array of unit cells may include dual-band or multi-band magnetic resonators. For example, two or more narrow-band excitations can be applied to the object using dual-band or multi-band magnetic resonators. In some embodiments, hyperspectral imaging is performed, in which measurements are performed across a desired electromagnetic spectrum. In an embodiment, the contrast of MIT images in biological tissues is almost entirely due to the (complex) electrical conductivity. At such low frequencies, complex conductivity, $\sigma_c = \sigma + i\omega\epsilon_r$, is predominantly real in living tissues, although its phase may vary significantly in other substances, such as rocks and soils. Multi-frequency, with several discrete excitation frequencies, or hyperspectral (e.g., broad-spectrum) versions of MIT, can provide a second contrast mechanism by mapping both the real and imaginary parts or, equivalently, the magnitude and phase of complex conductivity. In geophysical applications, magnetic susceptibility of the medium can be non-negligible due to the presence of iron and other magnetic elements, which enables additional contrast mechanisms. In an embodiment, a real dielectric constant can be obtained and used to discern non-conducting materials whose real dielectric constants are different. The array of unit cells can also sense a magnetic field at a plurality of frequencies or range of frequencies. In some embodiments, the plurality of frequencies may be a discrete plurality of frequencies. The plurality of frequencies may correspond to a discrete set of resonance frequencies of the unit cells. In some embodiments, the plurality of frequencies may be a continuous spectrum of frequencies.

The method further includes a control circuit determining a minimum of the first magnetic field (530). The minimum may correspond to a higher conductivity region of the target object. The control circuit can then adjust the excitation pattern based on the higher conductivity region of the target object (540). The method further includes comparing a difference between the conductivity map and the previous estimate of the conductivity map to a threshold value (545). For example, and similar to the methods described above with respect to method 300, method 500 may continue until a desired spatial resolution (e.g., threshold value) is obtained. The sequence can be terminated as soon as a certain level of confidence in the image reconstruction is obtained, or when the target spatial resolution is reached.

Figure 6:
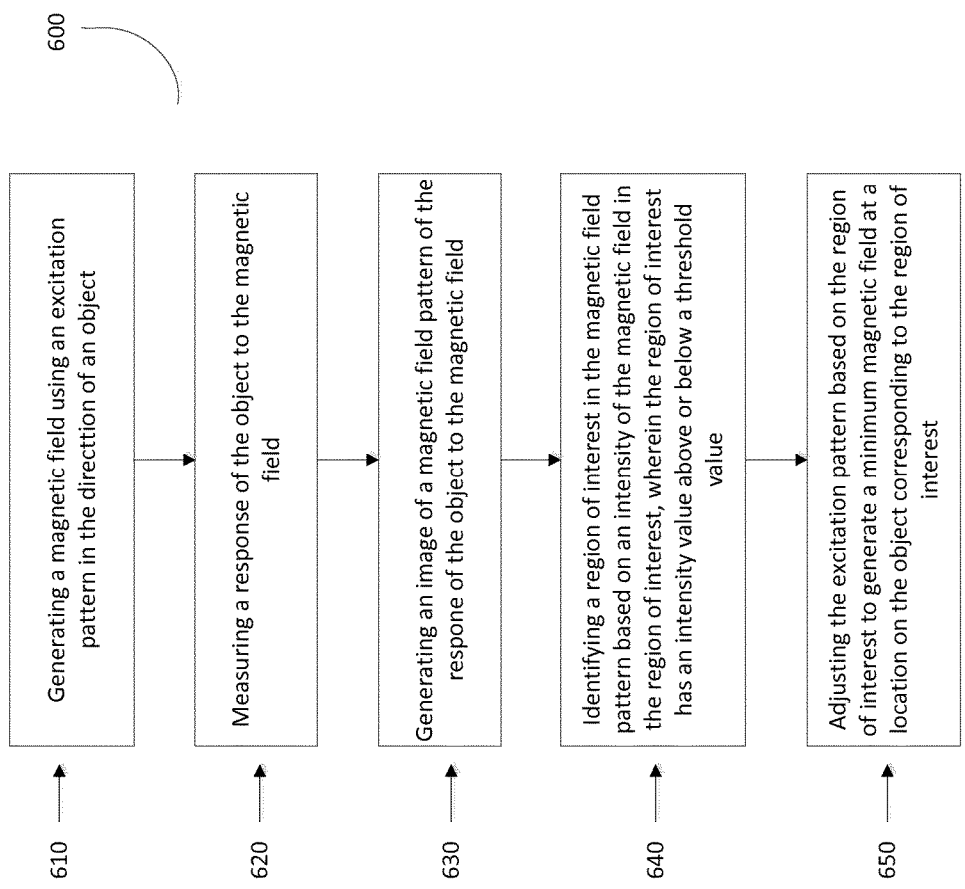
FIG. 6 is a flow diagram of a fourth method for performing magnetic induction tomography imaging of an object, according to one embodiment.

FIG. 6 depicts a flow diagram of a method 600 for imaging an object. In brief overview, the method includes an array of magnetic sources generating a magnetic field using an excitation pattern in the direction of an object (610) and measuring a response of the object to the magnetic field (620). The method further includes a control circuit generating an image of a magnetic field pattern of the response of the object to the magnetic field (630) and identifying a region of interest in the magnetic field pattern based on an intensity of the magnetic field in the region of interest, wherein the region of interest has an intensity value above or below a threshold value (640). The method further includes the control circuit adjusting the excitation pattern based on the region of interest to generate a minimum magnetic field at a location on the object corresponding to the region of interest (650).

In an embodiment, the method includes an array of unit cells generating a magnetic field using an excitation pattern in the direction of an object (610). The object may be a human organ or human tissue. The array of magnetic sources can be used for at least one of medical imaging, security imaging, or subsurface imaging.

Prior to generating a magnetic field, a control circuit communicatively coupled to the array of unit cells may determine the excitation pattern. The excitation pattern can be determined based on previous measurements, including at least one of a previously taken image of the object or an image selected from a library of images of similar objects. The control circuit may also determine an excitation current corresponding to the excitation pattern. Similar to the excitation pattern, the control circuit can calculate the excitation current using information and data obtained from previously taken image of the object or an image selected from a library of images. In other embodiments, the excitation pattern and the excitation current can be determined based on randomly selected values.

Once the excitation pattern has been determined, the control circuit can excite the array of unit cells using the excitation pattern. In some embodiments, the control circuit activates each unit cell in the array of unit cells simultaneously according to the excitation pattern. In other embodiments, each magnetic resonator can be activated at different and varying times according to the excitation pattern. Each unit cell can be activated with a different but non-vanishing amplitude.

The array of unit cells can generate a magnetic field having components in three mutually orthogonal directions in the direction of the object to be imaged. The magnetic field can be perpendicular to a plane of the array of unit cells. In some embodiments, the array of unit cells is multi-layered. For example, the array of unit cells may include two layers of unit cells, where a first layer of unit cells is stacked on top of a second layer of unit cells. The first layer can generate a first portion of the magnetic field perpendicular to a plane of the array of unit cells and the second layer can generate a second portion of the magnetic field orthogonal to a plane of the array of unit cells. Each layer of the two layers of unit cells can generate a portion of the magnetic field having components in three mutually orthogonal directions.

In some embodiments, the array of unit cells may include three or more layers of unit cells. The three or more layers can generate the magnetic field having components in three mutually orthogonal directions. In an embodiment, each layer of the three or more layers of unit cells can generate a portion of the magnetic field having components in three mutually orthogonal directions. The magnetic field is generated towards the object and a response to the magnetic field can be measured.

In an embodiment, the method includes an array of unit cells measuring a response of the object to the magnetic field (620). The array of unit cells can measure a gradient of three components of the magnetic field.

In some embodiments, the response is a magnetic flux value that indicates the amount of magnetic field passing through a given surface of the object. The magnetic flux value may be proportional to the number of magnetic field lines that pass through the surface of the object. For example, the magnetic flux value may be the number of magnetic field lines passing through the surface in one direction minus the number of magnetic field lines passing through in the other direction, such as the opposite direction.

In an embodiment, the measurements sensed by the array of unit cells can be transmitted and/or received by the control circuit coupled to the array. The control circuit can store the measurements and data associated with the response of the object to the magnetic field. Using the measurements, the control circuit can determine a magnetic flux value associated with the response of the object to the magnetic field. In an embodiment, the magnetic flux value can be based on a sensitivity matrix, for example, the sensitivity matrix described above with respect to FIG. 3A. The control circuit can determine a value for the sensitivity matrix that corresponds to the response of the object to the magnetic field.

In an embodiment, the method includes a control circuit generating an image of a magnetic field pattern of the response of the object to the magnetic field (630). The image may be generated using magnetic induction tomography and may identify electromagnetic properties of the object based on the applied magnetic field. The object or the surface of the object may have varying electromagnetic points at different points on the surface. The image can be of a magnetic field pattern made up conductivity voxels with varying values that correspond to the varying electromagnetic properties. In an embodiment, a voxel may represent a value in the image, for example, similar to a pixel. The control circuit can determine values for the conductivity voxels in the image. The control circuit can also determine a voxel conductivity score or total conductivity score, for the image of the magnetic field pattern. The voxel conductivity score may indicate a deviation from a previous image of the magnetic field pattern for the object.

In an embodiment, the method includes identifying a region of interest in the magnetic field pattern based on an intensity of the magnetic field in the region of interest. The region of interest can be identified based on having an intensity value above or below a threshold value (640). For example, using the conductivity voxel values, the control circuit can identify areas in the magnetic field pattern that either have a high conductivity value or a low conductivity value. In one embodiment, the region of interest may have the highest intensity or conductivity in the image of the magnetic field pattern. For example, a region of interest may be identified that has a highest conductivity voxel in the image. In some embodiments, a node in the magnetic field pattern may indicate a weakly conducting object. To image the object or at least image the regions or portions of the object that have weak conductivity with greater resolution, the image can be imaged again with a different excitation pattern.

In an embodiment, the method includes the control circuit adjusting the excitation pattern based on the region of interest to generate a minimum magnetic field at a location on the object corresponding to the region of interest (650). Adjusting the excitation pattern may include determining a second or new excitation pattern for imaging the object. The second excitation pattern can generate a minimum magnetic field at a location on the object corresponding to the region of interest. For example, the excitation pattern can provide a magnetic field distribution that puts a null or at least a minimum magnetic field on areas in the image corresponding to the highest conductivity values. For example, a portion of the surface of the object that was identified to have a high conductivity can be applied a different magnetic field of a different strength than an area identified to have a lower or weaker conductivity. The areas identified to have lower or weaker conductivity can be imaged with a lower signal to noise ratio and thus greater resolution. To determine if a point has a high or low conductivity, the voxel conductivity score corresponding to the point on the image can be compared to a pre-determined threshold value. In other embodiments, the determination is based on an average or analysis of the various voxel conductivity scores for an image. For example, the voxel conductivity scores can be ranked and the values in the top ten percent are considered to have high conductivity.

In an embodiment, the control circuit can excite the array of magnetic resonators with the second excitation pattern. The array of magnetic resonators can generate a second magnetic field using the second excitation pattern in the direction of the object and measure a second response of the object to the second magnetic field. The control circuit may generate a second image of a second magnetic field pattern of the second response of the object to the second magnetic field and identify a second region of interest in the second magnetic field pattern based on an intensity of the second magnetic field in the second region of interest. The control circuit may adjust the second excitation pattern based on the second region of interest. This process may continue until a conductivity map with a desired spatial resolution is obtained. To determine when a desired spatial resolution is obtained, a threshold value can be used.

For example, the control circuit may determine a second or new magnetic flux value for the object based on the second response of the object to the second magnetic field and update a conductivity map based on the second magnetic flux value.

In an embodiment, the voxel conductivity score for an image can be compared to a threshold value. The threshold value may indicate whether or not a new conductivity map provides a reliable or accurate estimate of a true conductivity map of the object. For example, the threshold value may correspond to a singular value decomposition or a spatial resolution of a previous image. When the conductivity score is greater than the threshold value, the conductivity map can be updated. Updating the conductivity map may include at least one of: changing a number of voxels in the conductivity map; changing dimensions of at least one voxel in the conductivity map; or changing a position of at least one voxel in the conductivity map. In other embodiments, if the conductivity score is equal to or less than the threshold value, the conductivity map is not updated. The comparison can identify the more accurate conductivity map. In an embodiment, the control circuit can output a final conductivity map when the voxel conductivity score is less than or equal to a threshold value.

In some embodiments, the control circuit can combine a two magnetic flux values for a comparison. For example, the control circuit can combine the second magnetic flux value and previous magnetic flux values associated with the object to create a test conductivity map. The updated conductivity map is compared to the test conductivity map and based on the results or differences between the two conductivity maps, the control circuit can update the conductivity map. In some embodiments, the control circuit can determine an optimum excitation current based on the updated conductivity map and the second magnetic flux value.

The construction and arrangement of the systems and methods as shown in the various embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the embodiments without departing from the scope of the present disclosure.

The present disclosure contemplates methods, systems and program products on any machine-readable media for accomplishing various operations. The embodiments of the present disclosure may be implemented or modeled using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. All such variations are within the scope of the disclosure. Likewise, software implementations could be accomplished with standard programming techniques with rule-based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. An apparatus for performing magnetic induction tomography enhanced with relaxation contrast imaging of a target object, comprising:
    an array of unit cells, wherein each unit cell includes a pattern of conducting lines, and wherein the array of unit cells is configured to generate a first magnetic field based on a first excitation pattern at a first time t and then sense a second magnetic field induced in the target object by the first magnetic field at at least one second time t+Δt; and
    a control circuit coupled to the array of unit cells, wherein the control circuit is configured to:
        determine a second excitation pattern corresponding to an estimated higher conductivity region of the target object having a higher conductivity relative to a remainder region of the target object, the higher conductivity region corresponding to a minimum of the first magnetic field; and
        provide, to the array of unit cells, the second excitation pattern to cause the array of unit cells to generate an adjusted first magnetic field based on the second excitation pattern.

2. The apparatus of claim 1, wherein the array of unit cells senses the second magnetic field at two or more times after the target object is excited by the first magnetic field.

3. The apparatus of claim 1, wherein the array of unit cells is configured to continuously generate the first magnetic field and continuously sense the second magnetic field induced in the target object.

4. The apparatus of claim 1, wherein the unit cells include a first set of unit cells configured to generate the first magnetic field and a second set of unit cells configured to sense the second magnetic field.

5. The apparatus of claim 1, wherein the array of unit cells is arranged in at least one of a planar formation, a curved formation, or a random formation.

6. The apparatus of claim 1, wherein the array of unit cells includes two layers of unit cells, wherein a first layer of unit cells is stacked on top of a second layer of unit cells.

7. The apparatus of claim 6, wherein the first layer of unit cells is configured to generate a first portion of the first magnetic field perpendicular to a plane of the array of unit cells, and wherein the second layer of unit cells is configured to generate a second portion of the first magnetic field orthogonal to a plane of the array of unit cells.

8. The apparatus of claim 1, wherein the array of unit cells includes three or more layers of unit cells, wherein the three or more layers of unit cells is configured to generate the first magnetic field having a predefined magnitude, direction, and phase.

9. The apparatus of claim 1, wherein a spatial resolution of the array of unit cells is based on a spacing between centroids of adjacent unit cells and dimensions of the unit cells.

10. The apparatus of claim 9, wherein the width of each of the conducting lines is greater than a skin depth of a corresponding conducting line at an operational frequency.

* * * * *